United States Patent
Imamura et al.

(10) Patent No.: US 10,525,132 B2
(45) Date of Patent: Jan. 7, 2020

(54) EXTERNAL AGENT FOR TREATING HYPERHIDROSIS

(71) Applicant: HISAMITSU PHARMACEUTICAL CO., INC., Tosu-shi, Saga (JP)

(72) Inventors: Kana Imamura, Tsukuba (JP); Tomohiro Shinoda, Tsukuba (JP); Shingo Somekawa, Tsukuba (JP); Yasunari Michinaka, Tsukuba (JP)

(73) Assignee: HISAMITSU PHARMACEUTICAL CO., INC., Tosu-Shi, Saga (JP)

( * ) Notice: Subject to any disclaimer, the term of this patent is extended or adjusted under 35 U.S.C. 154(b) by 0 days.

(21) Appl. No.: 15/568,432

(22) PCT Filed: Apr. 27, 2016

(86) PCT No.: PCT/JP2016/063188
§ 371 (c)(1),
(2) Date: Oct. 20, 2017

(87) PCT Pub. No.: WO2016/175240
PCT Pub. Date: Nov. 3, 2016

(65) Prior Publication Data
US 2018/0140704 A1    May 24, 2018

(30) Foreign Application Priority Data

Apr. 30, 2015  (JP) ................................. 2015-092946

(51) Int. Cl.
| | | |
|---|---|---|
| *A61K 47/12* | (2006.01) | |
| *A61K 31/216* | (2006.01) | |
| *A61P 17/00* | (2006.01) | |
| *A61K 9/00* | (2006.01) | |

(52) U.S. Cl.
CPC ............ *A61K 47/12* (2013.01); *A61K 9/0014* (2013.01); *A61K 31/216* (2013.01); *A61P 17/00* (2018.01)

(58) Field of Classification Search
None
See application file for complete search history.

(56) References Cited

U.S. PATENT DOCUMENTS

| | | | |
|---|---|---|---|
| 5,733,900 A | 3/1998 | Higo et al. | |
| 2003/0147926 A1* | 8/2003 | Ebert | A61K 9/0014 |
| | | | 424/400 |
| 2010/0137357 A1* | 6/2010 | Koleng | A61K 31/46 |
| | | | 514/304 |
| 2014/0037713 A1 | 2/2014 | Wotton et al. | |

FOREIGN PATENT DOCUMENTS

| | | |
|---|---|---|
| AU | 2012216593 B2 | 9/2012 |
| EP | 1170004 A1 | 1/2002 |
| EP | 0757910 B1 | 9/2002 |
| KR | 10-2012-0128522 A | 11/2012 |
| WO | 95/28914 A1 | 11/1995 |
| WO | 2007/046102 A2 | 4/2007 |
| WO | 2010/062930 A1 | 6/2010 |

OTHER PUBLICATIONS

Nature's Garden (Sodium Lactate in Soaps & Lotions, available online at http://www.naturesgardencandles.com/blog/sodium-lactate/, Sep. 26, 2013) (Year: 2013).*
International Preliminary Report on Patentability dated Oct. 31, 2017 issued in corresponding International Application No. PCT/JP2016/063188.
International Search Report dated Jul. 29, 2016 issued in corresponding International Application No. PCT/JP2016/063188.
Del Boz, "Systemic Treatment of Hyperhidrosis", ACTAS Dermo-Sifiliograficas, vol. 106, No. 4, Apr. 2015, pp. 271-277.
MacMillan F. S., et al, "The Antiperspirant Action of Topically Applied Anticholinergics", Journal of Investigative Dermatology, Elsevier, NL, vol. 43, Nov. 1, 1964, p. 363-377, XP009089620.
The Extended European Search Report dated Dec. 7, 2018 corresponding to application No. 16786516.1-1109.
Search Report dated Sep. 4, 2019 corresponding to European Application No. 16891597.3-1114.

* cited by examiner

*Primary Examiner* — Craig D Ricci
(74) *Attorney, Agent, or Firm* — Nath, Goldberg & Meyer; Joshua B. Goldberg

(57) ABSTRACT

The present invention provides a topical preparation for treating hyperhidrosis, comprising water, an anticholinergic drug, and one or more salts selected from the group consisting of lactate, tartrate, acetate and phosphate. Such a topical preparation comprises the above certain salt, thereby facilitating the accumulation of the anticholinergic drug in skin appendages.

6 Claims, 4 Drawing Sheets

EXTERNAL AGENT FOR TREATING HYPERHIDROSIS

This is a National Phase Application filed under 35 U.S.C. 371 as a national stage of PCT/JP2016/063188, filed Apr. 27, 2016, an application claiming the benefit of Japanese Application No. 2015-092946, filed Apr. 30, 2015, the content of each of which is hereby incorporated by reference in its entirety.

TECHNICAL FIELD

The present invention relates to a topical preparation for treating hyperhidrosis.

BACKGROUND ART

Methods that involve administering a topical composition comprising an anticholinergic drug such as oxybutynin have been proposed as methods for treating hyperhidrosis (Patent Literature 1 and Patent Literature 2).

CITATION LIST

Patent Literature

Patent Literature 1: U.S. Patent Application Publication No. 2014/0037713
Patent Literature 2: International Publication No. WO 2007/046102

SUMMARY OF INVENTION

Technical Problem

Anticholinergic drugs are drugs that inhibit acetylcholine from binding to a muscarinic acetylcholine receptor, and suppress parasympathetic nerves. Accordingly, the administration of anticholinergic drugs may cause side effects such as dry mouth.

Solution to Problem

The present inventors have considered that enhancing the accumulation of anticholinergic drugs in sweat glands, the skin appendages, is important for treating hyperhidrosis while suppressing the above side effects, and have intensively studied the consideration. As a result, the present inventors have discovered that certain salts enhance the accumulation of anticholinergic drugs in skin appendages, and thus have completed the present invention.

Specifically, the present invention provides a topical preparation for treating hyperhidrosis, comprising water, an anticholinergic drug, and one or more salts selected from the group consisting of lactate, tartrate, acetate and phosphate. The above anticholinergic drug may be oxybutynin or a pharmaceutically acceptable salt thereof. The above salt may be sodium lactate. The above topical preparation may be a liquid preparation. The above liquid preparation may be in a form of lotion.

Advantageous Effects of Invention

A topical preparation for treating hyperhidrosis according to the present invention comprises one or more salts selected from the group consisting of lactate, tartrate, acetate and phosphate. Therefore, the accumulation of the anticholinergic drug in skin appendages is high.

DESCRIPTION OF EMBODIMENTS

Figure 1:
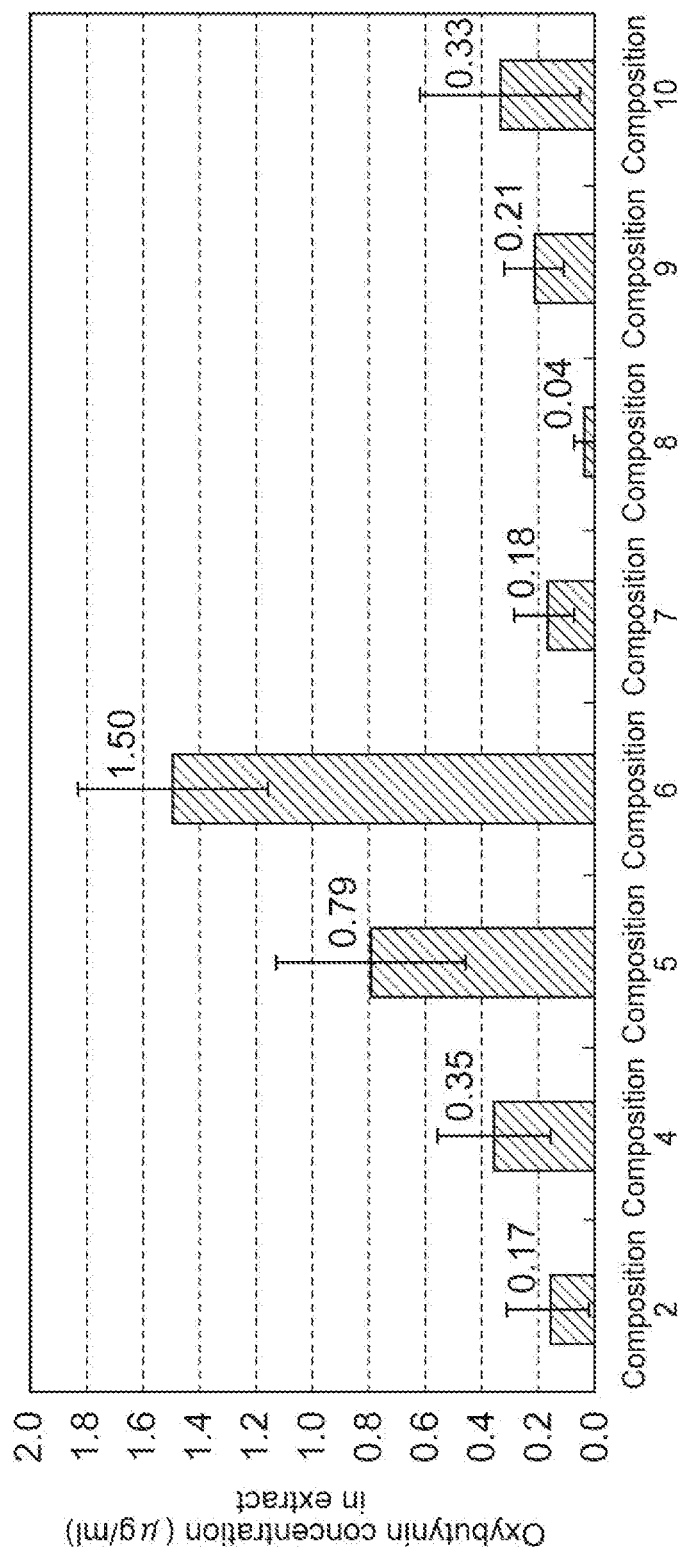
FIG. 1 is a graph showing the results of a test for examining the influence of salts in lotions on the accumulation of oxybutynin in porcine hair follicles.

Hereinafter, the present invention will be described more specifically with reference to an embodiment.

One embodiment of the present invention is a topical preparation for treating hyperhidrosis comprising water, an anticholinergic drug, and one or more salts selected from the group consisting of lactate, tartrate, acetate and phosphate.

The anticholinergic drug is not particularly limited, as long as it is a drug having anticholinergic effects, and examples thereof include oxybutynin, imidafenacin, trospium, tolterodine, glycopyrrolate, propantheline, benztropine, atropine, homatropine, tropicamide, benactyzine, biperiden, scopolamine, scopolamine butyl bromide, cyclopentolate, darifenacin, dexetimide, dicyclomine, emepronium, hexahydrosiladifenidol, octylonium, orphenadrine, oxyphenonium, pirenzepine, procyclidine, darotropium, ipratropium, tiotropium, oxitropium, quinidine, trihexyphenidyl, mivacurium, atracurium, doxacurium, cisatracurium, vecuronium, rocuronium, pancuronium, tubocurarine, gallamine, pipecuronium, trimethaphan, succinylcholine, suxamethonium, decamethonium and hexamethonium. From the viewpoint of accumulation in skin appendages, the anticholinergic drug is preferably oxybutynin or a pharmaceutically acceptable salt thereof. An example of the pharmaceutically acceptable salt of oxybutynin is oxybutynin hydrochloride.

The content of the anticholinergic drug may range from, for example, 0.5 to 35 mass %, or 0.5 to 15 mass %, based on the total mass of the topical preparation.

The topical preparation comprises one or more salts selected from the group consisting of lactate, tartrate, acetate and phosphate, thereby enhancing the accumulation of the anticholinergic drug in skin appendages. Such a salt may be anhydride or hydrate. Lactic acid may be either L- or D-lactic acid, or may be an arbitrary mixture thereof. Tartaric acid may be any one of L-, D-, and meso-tartaric acid, or may be an arbitrary mixture thereof. Examples of the salt include a salt with a monovalent metal such as sodium, potassium and lithium, a salt with a divalent metal such as calcium and magnesium, a salt with a trivalent metal such as aluminum, and a salt with an amine compound such as ammonia, ethylenediamine, triethylamine, diethanolamine, triethanolamine and meglumine. From the viewpoint of improving the accumulation of an anticholinergic drug in skin appendages, the salt is preferably lactate and more preferably sodium lactate.

The content of the above salt may range from, for example, 0.1 to 10 mass % based on the total mass of the topical preparation. The molar ratio of the anticholinergic drug to the above salt in the topical preparation may be, for example, within the range of 1:0.5 to 1:2.

The topical preparation for treating hyperhidrosis may be a liquid preparation, as well as a cream, a gel or an aqueous ointment, for example.

When the topical preparation for treating hyperhidrosis is a liquid preparation, water in the liquid preparation serves as a medium in which an anticholinergic drug and the above salt and other components are dissolved or dispersed. The content of water may range from, for example, 10 to 99 mass % based on the total mass of the liquid preparation.

Such a liquid preparation may comprise, in addition to the above components, a lower alcohol, a surfactant, a preservation stabilizer, a fat and oil, a solubilizer, a filler, a moisturizer, a pH regulating agent, an osmotic pressure regulator, a thickener, a refreshing agent, an astringent and a vasoconstrictor, for example.

The lower alcohol increases the solubility and dispersibility of the anticholinergic drug, and increases the distributivity of the anticholinergic drug into skin. Specific examples of the lower alcohol include methanol, ethanol and isopropanol. The content of the lower alcohol may range from, for example, 0 to 90 mass % based on the total mass of the liquid preparation.

The surfactant is useful for emulsifying the anticholinergic drug in a medium such as water. Specific examples of the surfactant include a nonionic surfactant (e.g., polysorbate 20, polysorbate 80, polysorbate 60, polyoxyethylene hydrogenated castor oil 20, polyoxyethylene hydrogenated castor oil 40 and polyoxyethylene hydrogenated castor oil 60), an ionic surfactant and an amphoteric surfactant. The content of the surfactant may range from, for example, 0 to 10 mass % based on the total mass of the liquid preparation.

Specific examples of the preservation stabilizer include a paraben, isopropylmethylphenol, phenoxyethanol and thymol.

Specific examples of the fat and oil and the solubilizer include a fatty acid, a fatty ester and a fatty alcohol.

Specific examples of the filler include an inorganic powder (e.g., talc, montmorillonite, smectite and kaolin) and an organic powder.

Specific examples of the moisturizer include a polyhydric alcohol, saccharides, urea, a vaseline and a paraffin.

The liquid preparation can have a pH within the range of 4.5 to 7.5. pH determination is performed using a composite glass electrode in accordance with "2.54 pH Determination" in General Tests, Processes and Apparatus, The Japanese Pharmacopoeia, Sixteenth Edition.

The liquid preparation may be in a form of lotion or liniment, for example, or in a form of embrocation or spray, for example, contained in appropriate containers (for example, spray containers for spraying the liquid preparation, containers for applying the liquid preparation and aerosol containers).

When the topical preparation for treating hyperhidrosis is a cream, water, the anticholinergic drug and the above salt may be contained in a cream base. The cream base is not particularly limited and may be selected from those generally used, such as a vaseline or a higher alcohol. To the cream base, for example, additives that are generally added to a cream, such as an emulsifier, a preservative, an absorption enhancer and a rash-preventing agent, may be added.

Moreover, a gelling agent and a neutralizer are added to a cream to adjust the pH to 4 to 8, so that a gelatinous cream can also be obtained. Such a gelatinous cream has intermediate properties between cream and gel. The water content in the cream may range from, for example, 0.5 to 70 mass % based on the total mass of the cream.

When the topical preparation for treating hyperhidrosis is a gel, water, the anticholinergic drug and the above salt may be contained in a gel base. The gel base is not particularly limited, and may be selected from those generally used, such as a higher alcohol. To the gel base, for example, additives that are generally added to a gel, such as a gelling agent, a neutralizer, a surfactant, an absorption enhancer, a solubilizer and a rash-preventing agent, may be added. Water content in the gel may range from, for example, 0.5 to 70 mass % based on the total mass of the gel.

When the topical preparation for treating hyperhidrosis is an aqueous ointment, water, the anticholinergic drug and the above salt may be dissolved or dispersed in a water-soluble base. The water-soluble base is not particularly limited and may be selected from those generally used, such as solid polyethylene glycol. To the water-soluble base, for example, additives that are generally added to an aqueous ointment, such as an absorption enhancer, a moisturizer and a rash-preventing agent, may be added. Water content in the aqueous ointment may range from, for example, 0.5 to 30 mass % based on the total mass of the aqueous ointment.

The topical preparation for treating hyperhidrosis can be manufactured by mixing thoroughly the above components.

After the container is shaken as necessary to thoroughly mix the components homogeneously, the topical preparation is applied to, sprinkled on or sprayed on the areas of skin where sweating should be decreased, and is spread as needed.

EXAMPLES

Test Example 1

Lotions were prepared according to the compositions in Table 1, and visually confirmed for the state of dissolution. Furthermore, the lotions were applied to porcine skin, and then the amounts of oxybutynin accumulated in hair follicles were measured by the following method.

1) 20 µL of a lotion was applied to 5 cm$^2$ of lightly shaved porcine skin. Number of pigs: n=3.

2) After 6 hours, the skin surface was cleaned with ethanol for disinfection, and washed with a stream of phosphate buffer, thereby removing oxybutynin that had adhered to the skin surface.

3) A hair follicle portion of 20 hairs was collected from the skin.

4) Oxybutynin was extracted from the hair follicles using 1 mL of an extracting liquid. As the extracting liquid, the following mobile phase was used.

5) Oxybutynin concentration was measured by high-performance liquid chromatography. Conditions for high-performance liquid chromatography were as follows.

Mobile phase: 0.1 w/w % aqueous phosphoric acid solution (containing 0.5 w/v % sodium dodecyl sulfate):acetonitrile=45:55 (v/v)

Flow rate: 1.5 mL/min

Column: TSK gel ODS-80 Ts (Tosoh Corporation)

Retention time: 10 minutes

TABLE 1

| | Composition | | | | | | | | | |
|---|---|---|---|---|---|---|---|---|---|---|
| | 1 | 2 | 3 | 4 | 5 | 6 | 7 | 8 | 9 | 10 |
| Oxybutynin | 4.54 | — | | | | | | | | |
| Oxybutynin hydrochloride | — | 5 | 5 | 5 | 5 | 5 | 5 | 5 | 5 | 5 |
| Sodium hydroxide | | | 0.51 | | | | | | | |
| Disodium hydrogenphosphate | | | | 0.9 | | | | | | |
| Sodium lactate | | | | | 1.42 | | | | | |
| Sodium acetate | | | | | | 1.04 | | | | |
| Disodium fumarate | | | | | | | 1.02 | | | |
| Trisodium citrate | | | | | | | | 1.09 | | |
| Sodium benzoate | | | | | | | | | 1.83 | |
| Disodium tartrate•dihydrate | | | | | | | | | | 2.92 |
| Ethanol | 40 | 40 | 40 | 40 | 40 | 40 | 40 | 40 | 40 | 40 |
| Others | 0.2 | 0.2 | 0.2 | 0.2 | 0.2 | 0.2 | 0.2 | 0.2 | 0.2 | 0.2 |
| Purified water | 55.26 | 54.8 | 52.49 | 53.9 | 53.38 | 58.76 | 53.78 | 53.71 | 52.97 | 51.88 |
| Total | 100 | 100 | 100 | 100 | 100 | 100 | 100 | 100 | 100 | 100 |

Results are shown in Table 2 and FIG. 1. With the lotion comprising phosphate, lactate, acetate or tartrate, the accumulation of oxybutynin in hair follicles was high, compared to lotions comprising none of the above salts.

TABLE 2

| Composition | 1 | 2 | 3 | 4 | 5 | 6 | 7 | 8 | 9 | 10 |
|---|---|---|---|---|---|---|---|---|---|---|
| State of dissolution | X | X | X | ○ | ○ | ○ | ○ | ○ | ○ | ○ |

○: Dissolved to be a clear liquid.
X: Insoluble matter was observed.

Test Example 2

Lotions were prepared according to the compositions in Table 3. The lotions were determined for the effect of decreasing sweating by a pilocarpine-induced sweat test. Moreover, in a manner similar to that in test example 1, the lotions were applied to porcine skin, and then oxybutynin concentrations were measured.

The pilocarpine-induced sweat test was conducted by the following method.

1) A lotion was diluted 12-fold with a 40 mass % aqueous ethanol solution.
2) 10 μL or 15 μL of the lotion was applied to about 0.5 cm² of a mouse footpad. Number of mice: n=5 to 6.
3) After 4 hours, iodine and a starch solution were applied to the footpad under anesthesia.
4) Pilocarpine was intradermally administered at 5 μg/foot.
5) After 5 minutes, the number of black spots resulting from the iodostarch reaction was counted.

TABLE 3

| | Composition | | | | |
|---|---|---|---|---|---|
| | 11 | 12 | 13 | 14 | 15 |
| Oxybutynin hydrochloride | 0 | 1 | 2.5 | 5 | 10 |
| Lactic acid | 2.29 | | | | |
| Sodium chloride | 1.48 | | | | |
| Sodium lactate | | 0.28 | 0.71 | 1.42 | 2.84 |

TABLE 3-continued

| | Composition | | | | |
|---|---|---|---|---|---|
| | 11 | 12 | 13 | 14 | 15 |
| Ethanol | 40 | 40 | 40 | 40 | 40 |
| Others | 2 | 2 | 2 | 2 | 2 |
| Purified water | 54.23 | 56.72 | 54.79 | 51.58 | 45.16 |
| Total | 100 | 100 | 100 | 100 | 100 |

Figure 2:
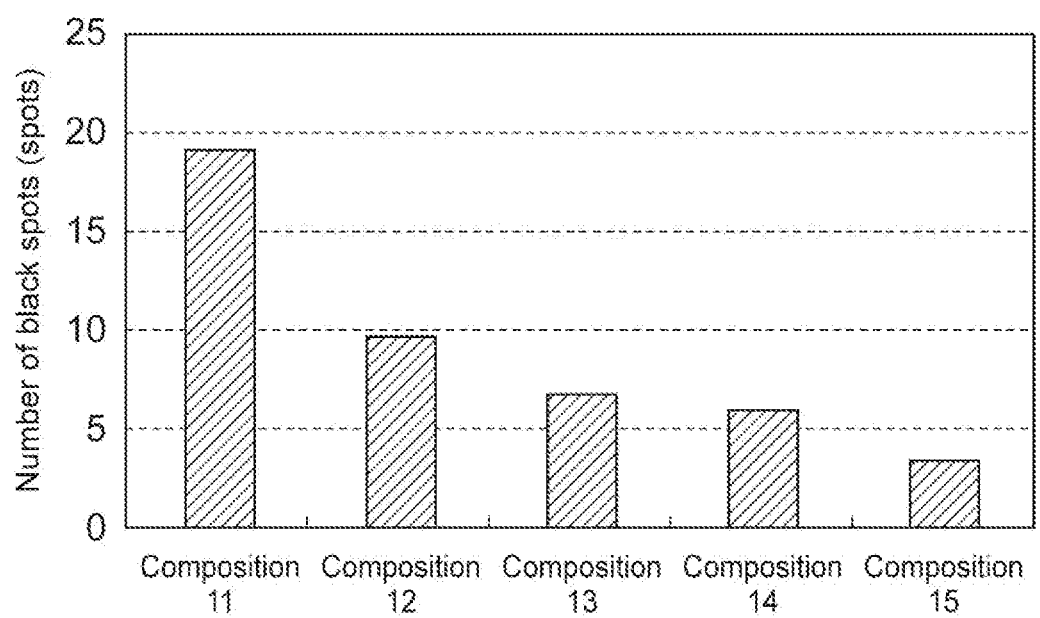
FIG. 2 is a graph showing the results of a test for examining the influence of the concentrations of oxybutynin in lotions on the effect of decreasing sweating.
Figure 3:
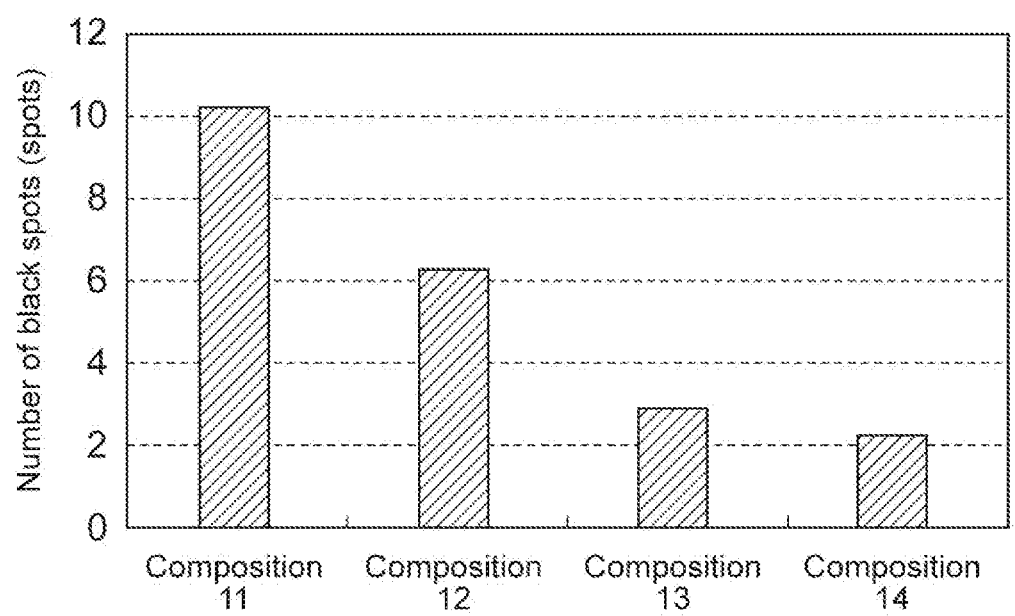
FIG. 3 is a graph showing the results of a test for examining the influence of the concentrations of oxybutynin in lotions on the effect of decreasing sweating.
Figure 4:
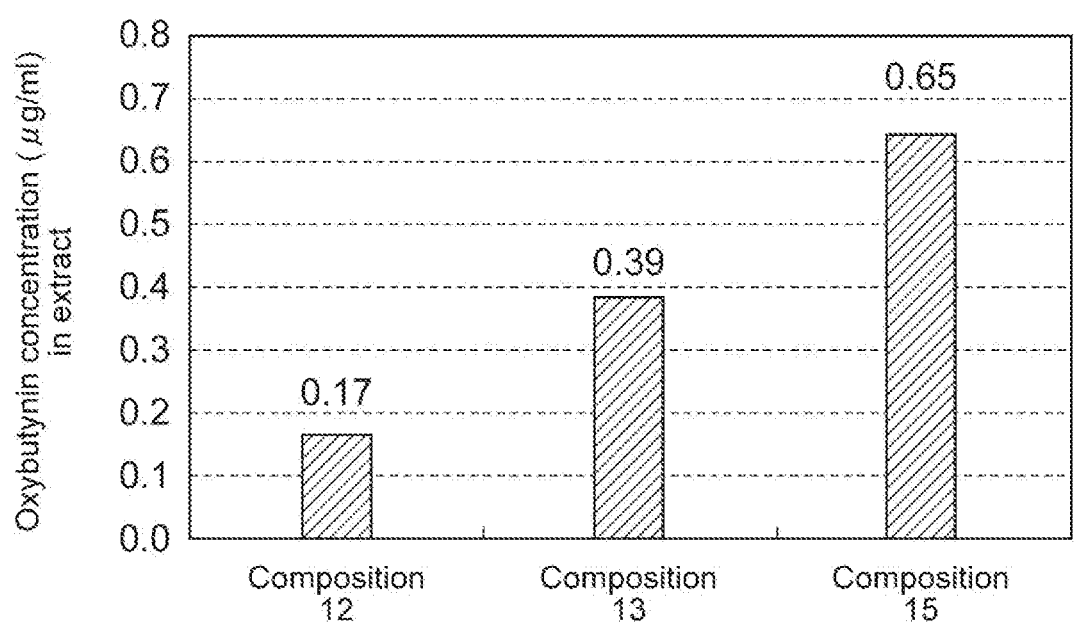
FIG. 4 is a graph showing the results of a test for examining the influence of the concentrations of oxybutynin in lotions on the accumulation of oxybutynin in porcine hair follicles.

Results are shown in FIG. 2 to FIG. 4. FIG. 2 shows the results of the pilocarpine-induced sweat test when the amount of each lotion applied was 10 μL, and FIG. 3 shows the results of the pilocarpine-induced sweat test when the amount of each lotion applied was 15 μL. It was confirmed that the lotions' effect of decreasing sweating was oxybutynin concentration-dependent. It was also confirmed that the amounts of oxybutynin accumulated in hair follicles were oxybutynin concentration-dependent.

Test Example 3

Lotions were prepared according to the compositions in Table 4. The lotions were determined for the effect of decreasing sweating by the pilocarpine-induced sweat test.

The pilocarpine-induced sweat test was conducted by the following method.

1) A lotion was diluted 12-fold with a 40 mass % aqueous ethanol solution.
2) 10 μL of the lotion was applied to about 0.5 cm² of a mouse footpad.

Number of mice: n=6.

3) After 3 hours, the footpad was washed, the mouse was left to stand for 1 hour, and then iodine and a starch solution were applied to the footpad under anesthesia.
4) Pilocarpine was intradermally administered at 15 μg/foot.
5) After 5 minutes, the number of black spots resulting from the iodostarch reaction was counted.

TABLE 4

| | Composition | | | |
|---|---|---|---|---|
| | 16 | 17 | 18 | 19 |
| Oxybutynin | | | | 2.27 |
| Oxybutynin hydrochloride | | 2.5 | 2 | |
| Sodium lactate | | 0.71 | | |
| Sodium acetate | | | 0.42 | |
| Lactic acid | 0.57 | | | |
| Sodium chloride | 0.37 | | | |
| Ethanol | 40 | 40 | 40 | 40 |
| Purified water | 59.056 | 56.79 | 57.584 | 57.73 |
| Total | 100 | 100 | 100 | 100 |

Results are shown in Table 5. The lotion comprising lactate or acetate exerted a stronger effect of decreasing sweating than the salt-free lotions.

TABLE 5

| | Number of black spots | |
|---|---|---|
| Composition | Mean value | Standard error |
| 16 | 22.0 | 4.4 |
| 17 | 4.5 | 1.9 |
| 18 | 3.2 | 0.9 |
| 19 | 10.8 | 1.8 |

The invention claimed is:

1. A topical preparation for treating hyperhidrosis, comprising:
water;
a lower alcohol;
0.5 to 35 wt. % oxybutynin or a pharmaceutically acceptable salt thereof; and
one or more salts selected from the group consisting of 0.71 to 10 wt. % lactate and 0.42 to 10 wt. % acetate.

2. A topical preparation for treating hyperhidrosis comprising:
water;
a lower alcohol;
0.5 to 35 wt. % oxybutynin or a pharmaceutically acceptable salt thereof; and
0.71 to 10 wt. % sodium lactate.

3. The topical preparation according to claim 1, wherein the topical preparation is a liquid preparation.

4. The topical preparation according to claim 3, wherein the liquid preparation is in a form of lotion.

5. The topical preparation according to claim 2, wherein the topical preparation is a liquid preparation.

6. The topical preparation according to claim 5, wherein the liquid preparation is in a form of lotion.

\* \* \* \* \*